United States Patent [19]

Schryvers

[11] Patent Number: 5,141,743
[45] Date of Patent: Aug. 25, 1992

[54] METHOD FOR ISOLATING AND PURIFYING TRANSFERRIN AND LACTOFERRIN RECEPTOR PROTEINS AND VACCINES CONTAINING THE SAME

[75] Inventor: Anthony B. Schryvers, Calgary, Canada

[73] Assignee: University Technologies International, Inc., Calgary, Canada

[21] Appl. No.: 639,365

[22] Filed: Jan. 10, 1991

Related U.S. Application Data

[63] Continuation of Ser. No. 344,356, Apr. 27, 1989, abandoned.

[51] Int. Cl.$^5$ .................. C07K 15/14; A61K 39/02
[52] U.S. Cl. ........................... 424/92; 530/400; 530/350; 530/395; 530/413
[58] Field of Search ............... 530/350, 395, 413, 400; 424/92

[56] References Cited

U.S. PATENT DOCUMENTS

| | | | |
|---|---|---|---|
| 4,434,156 | 2/1984 | Trowbridge | 424/85 |
| 4,447,547 | 5/1984 | Allen et al. | 436/543 |

OTHER PUBLICATIONS

Schryvers, A. B. et al., 1988, Mol. Microbiol. 2(2): 281–288 (abstract).
Lee et al., 1988, Mol. Microbiol. 2(6): 827–829 (abstract).
Schryvers et al., "Comparative Analysis of the Transferrin and Lactoferrin Binding Proteins in the Family Neisseriaceae", Can J. Microbiol., vol. 35, 1989, pp. 409–415.
Lee et al., "Specificity of the Lactoferrin and Transferrin Receptors in Neisseria Gonorrhoeae", Molecular Microbiology, (1988) 2(6), 827–829.
Abstract, Ala'Aldeen, D. A., Heather A. Davies, Wall, R. A., and Borriello, S. P., "Interaction Between Iron Regulated Outer Membrane Proteins of Neisseria Meningitidis and Human Transferrin Binding Activity".
Selected Pages from the Thesis of Leigh J. Morris, 1988, at the University of Calgary "Meningococcal Receptors for Transferrins".
*Identification and Characterization of the Human Lactoferrin-Binding Protein from Neisseria Meningitidis*, Schryvers and Morris, Infection and Immunity, May 1988, pp. 1144–1149.
*Characterization of the Human Transferrin and Lactoferrin Receptors in Haemophilus Influenzae*, Schryvers, Molecular Microbiology (1988) 2(4), pp. 467–472.
*Identification of the Transferrin— and Lactoferrin-Binding Proteins in Haemophilus Influenzae*, Schryvers, J. Med. Microbiol., vol. 29, (1989), pp. 121–130.
*Comparison of the Abilities of Different Protein Sources of Iron to Enhance Neisseria Meningitidis Infection in Mice*, Schryvers and Gonzalez, Infection and Immunity, Aug. 1989, pp. 2425–2429.

Primary Examiner—Robert A. Wax
Assistant Examiner—Keith C. Furman
Attorney, Agent, or Firm—Burns, Doane, Swecker and Mathis

[57] ABSTRACT

The present invention relates to a method for isolating and purifying transferrin and lactoferrin receptor proteins from bacterial pathogens by affinity chromatography and to vaccine antigens containing the purified receptor proteins.

15 Claims, 1 Drawing Sheet

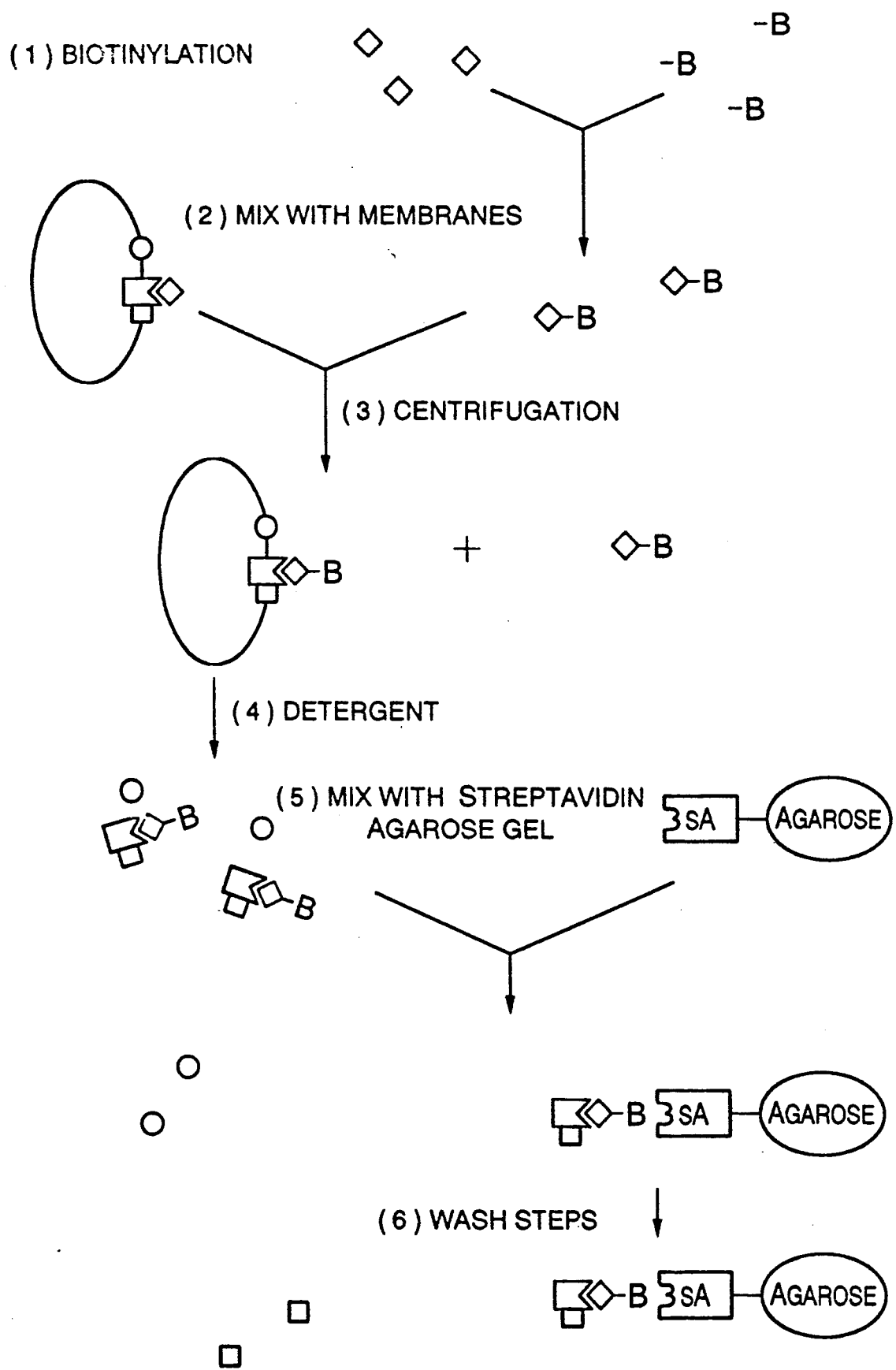

METHOD FOR ISOLATING AND PURIFYING TRANSFERRIN AND LACTOFERRIN RECEPTOR PROTEINS AND VACCINES CONTAINING THE SAME

This application is a continuation of application Ser. No. 07/344,356, filed Apr. 27, 1989, now abandoned.

BACKGROUND OF THE INVENTION

The present invention relates to a method for isolating and purifying transferrin and lactoferrin receptor proteins from bacterial pathogens and to vaccines containing purified transferrin and/or lactoferrin receptor proteins.

There are a number of important bacterial pathogens causing disease in humans and in animals for which effective vaccines are either absent or unsatisfactory. A number of these pathogens are relatively host specific with respect to their ability to cause natural infection. Bacteria such as Neisseria meningitidis, Haemophilus influenzae and Neisseria gonorrhoeae continue to be an important cause of endemic and epidemic human diseases such as meningitis, otitis, epiglottitis, gonorrhea and urethritis. Similarly, Pasteurella haemolytica, Haemophilus somnus and Pasteurella multocida are important causative agents of pneumonic pasteurellosis and infectious thromboembolic meningoencephalitis in cattle. In pigs, Actinobacillus (Haemophilus) pleuropneumoniae is an important causative agent of infectious pneumonia.

Haemophilus influenzae and Neisseria meningitidis are the most common cause of bacterial meningitis in young children. Despite available effective antibiotic therapy, significant mortality and morbidity result from meningococcal infection. The fulminant nature of the infection, coupled with the scant characteristic clinical signs present in children under two years of age, may be a major factor contributing to continuing mortality and morbidity.

Vaccines based on the capsular polysaccharide of the Neisseria meningitidis bacterium were developed after a correlation was observed between the presence of anticapsule antibody and resistance to systemic meningococcal infections. These capsular polysaccharide vaccines are effective against infection caused by organisms from the A, C, Y, and W-135 capsular serogroups of meningococci. However, no effective vaccine is available against the most common serogroup B meningococci. There is a poor humoral response to the capsular polysaccharide vaccines in children less than two years of age who are at the highest risk of infection from endemic disease. Further, capsular vaccines do not provide immunological memory and the duration of immunity is relatively short. Although attempts to overcome the poor immunogenicity by chemical modification and conjunction to tetanus toxoid show some promise, the results have to be considered in light of the demonstrated serological cross-reactivity of serogroup B capsule with human fetal and infant neural tissue. In view of this consideration, development of a polyvalent polysaccharide vaccine that provides sufficiently broad coverage for prevention of endemic meningococcal disease seems unlikely.

Neisseria gonorrhoeae causes gonorrhea which is plaguing the world in epidemic proportions. Development of a gonococcal vaccine is of a high priority.

Bovine pneumonic pasteurellosis, a major cause of economic loss to the cattle industry, is primarily due to Pasteurella haemolytica. The experimental studies and field trials with vaccines containing P. haemolytica have been inconsistent in reducing the incidence and severity of the disease. Infectious thromboembolic meningoencephalitis, an important cause of mortality in feedlot cattle, is caused by Haemophilus somnus. There is currently no effective vaccine for the prevention of this disease. Actinobacillus (Haemophilus) pleuropneumonia causes a contagious pneumonia in pigs which constitutes a major problem for the swine industry throughout the world. Vaccination with crude vaccine preparations have not been successful due to limited protection of heterologous serotypes.

Iron acquisition is essential for the growth and survival of bacterial pathogens in the host and for causing infection. Bacterial pathogens in the mammalian host are confronted with an environment in which the level of iron is extremely low. In the extracellular compartment, iron is sequestered by the proteins transferrin and lactoferrin, which predominate in serum and mucosal secretions, respectively. The ability to compete with lactoferrin and transferrin for iron is thought to be essential for the pathogenesis of many bacterial infections. Most bacteria manufacture iron-chelating compounds known as siderophores to facilitate iron acquisition from their environment. However, several pathogenic bacteria, such as Neisseria meninoitidis, Neisseria gonorrhoeae, and Haemophilus influenzae do not produce siderophores, but rather acquire lactoferrin iron and transferrin iron directly for growth in vitro.

Early observations of meningococci and gonococci by B. E. Holbein, I. W. DeVoe and F. P. Sparling and co-workers demonstrated that these bacteria can grow in the presence of transferrin or lactoferrin proteins and can use iron from these proteins as the sole source of iron for growth. It was further established that separation of the proteins from the cells with a dialysis membrane excluded the use of transferrin or lactoferrin iron, indicating that soluble factors removing iron from lactoferrin or transferrin were not involved, thus suggesting that cell contact was necessary. Studies by F. P. Sparling and D. W. Dyer have demonstrated that mutants specifically deficient in iron acquisition from transferrin are deficient in binding.

The mechanism of iron acquisition from transferrin and lactoferrin has not previously been studied in the bacteria Pasteurella haemolytica, Haemophilus somnus, Pasteurella multocida, Actinobacillus (Haemophilus) pleuropneumoniae or Haemophilus suis.

By virtue of their functions, the transferrin and lactoferrin receptor proteins are located on the surface of the bacteria when in the host and are accessible to large proteins. Thus, the receptors would be accessible to antibody-mediated host defenses. The transferrin and lactoferrin protein receptors are essential for obtaining iron for growth and for survival. Thus, the pathogen cannot lose its transferrin and/or lactoferrin receptors to evade immunity provided by vaccine antigens containing such receptor proteins. Any attempt at such a evasive technique would result in an inability to survive in the host.

The nature of the iron uptake process was not previously known, and identification and characterization of the lactoferrin and transferrin receptor proteins have not previously been possible. Nor have the lactoferrin and transferrin receptor proteins previously been isolated and purified. Further, no vaccine containing the receptor proteins has been previously developed.

SUMMARY OF THE INVENTION

The present invention overcomes the problems and disadvantages of the prior art by providing a method for isolating and purifying the lactoferrin and transferrin receptor proteins thereby facilitating the production of vaccines containing the lactoferrin and/or transferrin receptor proteins.

It is an object of the invention to provide a method for identifying lactoferrin and transferrin receptor proteins in bacterial pathogens and isolating and purifying the same.

It is also an object of the invention to provide single component vaccine antigens that are effective in the prevention of diseases caused by bacterial pathogens containing lactoferrin and transferrin receptor proteins.

It is a further object of the invention to provide vaccine antigens that are effective in preventing bacterial pathogen diseases in young children.

It is an additional object of the invention to provide vaccine antigens that exhibit superior immunological memory to current polysaccharide capsular vaccines.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

To achieve the objects and in accordance with the purpose of the invention, as embodied and broadly described herein, the present invention provides a method for isolating and purifying lactoferrin and transferrin binding proteins in membrane preparations from strains expressing lactoferrin and/or transferrin binding activity by affinity chromatography.

The present invention also provides vaccine antigens containing a preparation of purified lactoferrin and/or transferrin receptor proteins.

A lactoferrin receptor vaccine antigen is provided comprising a preparation selected from the group consisting of (1) a purified lactoferrin receptor protein isolated from a bacterium or an organism expressing a cloned lactoferrin receptor gene, (2) a derivative of a purified lactoferrin receptor protein, (3) a fusion protein containing all or part of a coding sequence of a lactoferrin receptor gene, and (4) a synthetic peptide whose amino acid sequence is based on the amino acid sequence of a purified lactoferrin receptor or on the nucleotide sequence of a cloned receptor gene. The preparation is typically suspended in 0.15 M sodium chloride, 0.05 M sodium phosphate, a buffer having a pH of about 7.4, "MERTHIOLATE", a trademark for thimersal and optionally, an adjuvant.

The invention also provides a transferrin receptor vaccine antigen comprising a preparation selected from the group consisting of (1) one or more purified transferrin receptor proteins isolated from a bacterium or an organism expressing at least one cloned transferrin receptor gene, (2) a derivative of a purified transferrin receptor protein, (3) a fusion protein containing all or part of a coding sequence of at least one transferrin receptor gene, and (4) a synthetic peptide whose amino acid sequence is based on the amino acid sequence of a purified transferrin receptor protein or on the nucleotide sequence of a cloned receptor gene. The preparation may be suspended in 0.15 M sodium chloride, 0.05 M sodium phosphate, a buffer having a pH of about 7.4, "MERTHIOLATE" and optionally, an adjuvant. The single-component vaccine antigens of the invention are effective against bacterial pathogens that acquire iron directly through transferrin and/or lactoferrin receptors. The vaccine antigens are also suitable for providing immunity to young children.

The accompanying drawing, which is incorporated in and constitutes a part of this specification, illustrates an embodiment of the invention, and together with the description, serves to explain the principles of the invention.

BRIEF DESCRIPTION OF THE DRAWINGS

The drawing is a flow chart of an affinity chromatography method according to the present invention.

DESCRIPTION OF THE PREFERRED EMBODIMENTS

Reference will now be made in detail to the present preferred embodiments of the invention.

The lactoferrin receptor is a surface-accessible outer membrane protein. It has been found to have a molecular weight of about 106,000 in *Neisseria gonorrhoeae* and *Neisseria meningitidis*. The receptor is specific for binding lactoferrin. It does not bind transferrin or any other iron-binding proteins. Further, the receptor from *Neisseria* and *Branhamella* species binds human lactoferrin with high affinity but does not specifically bind lactoferrin from other species. Expression of the receptor is regulated by the level of iron available to the bacteria possessing the receptor. In the presence of ample iron, very little protein is produced. When iron is limited, there is a large increase in the amount of receptor protein produced. The receptor will not mediate iron acquisition or iron-dependent growth from lactoferrin obtained from other species. It binds iron-saturated human lactoferrin and human apolactoferrin with equal affinity. The lactoferrin receptor in *Neisseria meningitidis* has been found to bind the following lactoferrin receptor specific monoclonal antibodies: Nos. 33-15-4, 33-188-2, 33-75-6, 33-36-16 and 33-19-3.

The transferrin receptor is composed of proteins whose expression are also regulated by the level of iron available to the bacteria possessing the receptor. In the presence of ample iron, very little protein is produced. When iron is limited, there is a dramatic increase in the amount of receptor proteins produced. The transferrin receptor in the human pathogens *Neisseria meningitidis, Neisseria gonorrhoeae, Haemophilus influenzae* and *Branhamella catarrhalis*, will mediate iron acquisition and iron-dependent growth from human transferrin but not from transferrins obtained from other species. In cattle pathogens *Pasteurella haemolytica, Haemophilus somnus,* and *Pasteurella multocida*, the transferrin receptor will mediate iron-dependant growth from bovine transferrin but not from transferrins obtained from other species. In pig pathogens *Actinobaccilus pleuropneumoniae, Actinobacillus suis,* and *Haemophilus suis,* the transferrin receptor will mediate iron-dependant growth from porcine transferrin but not from transferrin obtained from other species.

The transferrin receptor consists of two outer membrane proteins: (1) a higher molecular weight protein of about 100,000 in *Neisseria meningitidis, Neisseria gonorrhoeae* and *Haemophilus influenzae*; and (2) a lower molecular weight protein of from about 65,000 to about 90,000 in various strains and species. The lower molecular weight protein can partially reconstitute transferrin binding activity after sodium dodecyl sulfate polyacrylamide electrophoresis and electroblotting. Both purified receptor proteins can partially reconstitute transferrin binding activity after elution from an affinity column with guanidine hydrochloride and removal of the guanidine hydrochloride.

The transferrin receptor binds transferrin but not other iron-binding proteins. In the human pathogens *Neisseria meningitidis, Neisseria gonorrhoeae, Branhumella catarrhalis* and *Haemophilus influenzae*, the receptors bind human transferrin with high affinity but do not specifically bind transferrin from other species. In the bovine pathogens *Pasteurella haemolytica, Haemophilus somnus,* and *Pasteurella multocida*, the receptors bind bovine transferrin but not transferrins from other species. In the pig pathogens *Actinobacillus pleuropneumoniae, Actinobacillus suis,* and *Haemophilus suis*, the receptors bind porcine transferrin but not transferrins from other species. The transferrin receptor from human pathogens binds iron-saturated human transferrin with about ten-fold higher affinity than with which it binds human apotransferrin and binds partially and fully deglycosylated human transferrin with equal affinity but does not bind human transferrin treated with mild periodate oxidation. The transferrin receptor binds the following monoclonal antibodies: Nos. 36-4, 36-6, 36-104 and 32-58-5.

Lactoferrin-binding activity in several *Neisseria meningitidis* strains, *N. gonorrhoeae, N. lactamica* and *B. catarrhalis* was determined using a solid phase binding assay with horseradish peroxidase-conjugated human lactoferrin or alternatively by using biotinylated human lactoferrin followed by horseradish peroxidase-conjugated streptavidin. Lactoferrin-binding activity was found to exist in all meningococcal strains tested. The expression of lactoferrin-binding activity closely parallels the expression of transferrin-binding activity. Binding is specific for human lactoferrin. Neither bovine lactoferrin, human transferrin, nor human hemoglobin block binding of horseradish peroxidase-conjugated human lactoferrin. Binding of lactoferrin is not dependent on the level of iron saturation since iron-saturated lactoferrin and apolactoferrin are equally effective at blocking binding of HRP-lactoferrin in competitive binding assays.

The lactoferrin-binding protein has been identified by batch affinity chromatography with biotinylated human lactoferrin and streptavidin-agarose in several bacterial strains. Biotinylated lactoferrin was bound to intact total membranes and then was separated from free lactoferrin by centrifugation. The lactoferrin receptor complex was then solubilized from the membranes, separated from unsolubilized material and bound to a streptavidin-agarose resin by virtue of the biotin moiety attached to lactoferrin. After washing the resin, the bound proteins were eluted by boiling in sample buffer and analyzed by SDS-PAGE. Alternatively, the lactoferrin receptor protein can be eluted by increasing concentrations of guanidine hydrochloride.

A protein having a molecular weight of about 105,000 was bound to the lactoferrin affinity resin when total membrane from iron-starved *N. meningitidis* B16B6, Group X and Group W135 was used.

The mechanism of iron acquisition from transferrin in meningococci involves binding by a receptor on the surface of the bacterium, and the lack of accumulation of $^{125}$I-transferrin indicates that uptake is not due to internalization of a transferrin-receptor complex. It is believed that the removal of iron from transferrin and the release of apotransferrin are subsequent steps in the uptake mechanism. There is a higher affinity of the transferrin receptor for iron-saturated transferrin than for apotransferrin. Since iron acquisition from lactoferrin also involves a surface receptor, it is believed that a similar mechanism of uptake exists for lactoferrin receptors.

Transferrin-binding activity was detected in all strains of *Neisseria meningitidis, Haemophilus influenzae. N. gonorrhoeae, N. lactamica* and *B. catarrhalis* tested. Transferrin binding activity in all isolates tested was specific for human transferrin in that only human transferrin could effectively block binding of horseradish peroxidase human transferrin.

The transferrin receptor was previously identified by SDS-PAGE and Western blot analysis as a protein having a molecular weight of from about 75,000 to about 88,000. However, a pure transferrin receptor was not isolated by that procedure. Also, the higher molecular weight transferrin binding protein was not identified by that procedure. The inventor discovered that isolation of pure transferrin receptor is achieved by affinity chromatography with biotinylated transferrin and streptavidinagarose. Transferrin-binding proteins having a lower molecular weight ranging from about 58,000 to about 98,000 and a higher molecular weight protein of from about 94,000 to about 106,000 were isolated in the above strains. In the family *Neisseriaceae*, affinity isolation with biotinylated transferrin yielded at least two proteins in all species tested, the higher molecular weight protein being about 98 kd in all isolates of *Neisseria* and about 105 kd in *B. catarrhalis*.

The present inventor has found that the human transferrin receptor is present in all *Haemophilus influenzae* isolates tested, but is not detectable in other *Haemophilus* species or in the representative isolates from the genera *Pasteurella* or *Actinobacillus*. The absence of the transferrin receptor in other *Haemophilus* species and in *Actinobacillus* and *Pasteurella* may be pertinent to the reason why these bacteria rarely cause invasive disease in humans. Similarly, the inventor has detected a bovine transferrin receptor in all isolates of *Pasteurella haemolytica* and *Haemophilus somnus* tested and in some of the isolates of *Pasteurella multocida*. Also, the inventor has detected porcine transferrin binding in all isolates of *Actinobacillus pleuropneumoniae* tested. Therefore, the presence of receptor correlates well with the ability of these organisms to cause disease in their receptive hosts.

The vaccine antigen of the invention can be prepared from lactoferrin and/or transferrin receptor protein isolated from bacterial pathogens causing disease. If a preparation is found not to be sufficiently immunogenic, an appropriate adjuvant, such as aluminum hydroxide, may be included in the vaccine preparation.

The lactoferrin and/or transferrin receptor protein isolates are included in the vaccine antigens of the invention in a pharmaceutically effective amount to achieve sufficient immunogenicity.

The vaccine antigens of the invention can be administered by an effective route of administration well known to those of ordinary skill in the art, for example, subcutaneously or intramuscularly.

The invention will be further clarified by the following examples which are intended to be purely exemplary of the invention.

EXAMPLE 1

Identification And Characterization Of The Human-Lactoferrin Binding Protein From Neisseria Meningitidis Bacterial strains and growth conditions

*N. meninoitidis* B16B6, a standard serotyping strain was obtained from C. Frasch. Group X and group W135 meningococcal strains were obtained from Foothills Hospital, Calgary, Alberta. Meningococci were grown on chocolate agar plates supplemented with CVA enrichment (GIBCO Laboratories, Grand Island, N.Y.) in an atmosphere containing 5% $CO_2$. Freshly grown cells from chocolate plates were routinely used to inoculate liquid Mueller-Hinton broth (MHB) to a starting A600 of 0.04 and were incubated with shaking for 16 hours prior to harvest. Iron starvation MHB normally contained 35 $\mu$M EDDA (ethylenediamine di-ortho-hydroxyphenylacetic acid). The broth and culture conditions used for expression experiments are indicated in Table 1.

Chemicals

Horseradish peroxidase-conjugated human lactoferrin was obtained from Jackson Immunoresearch Laboratories, Avondale, Pa. Bovine lactoferrin was from Accurate Chemicals, Westbury, N.Y. Human lactoferrin (L-8010), human transferrin (T2252), and human hemoglobin (H7379) were from Sigma Chemical Co., St. Louis, Mo. Biotin-X-NHS (biotinyl-$\epsilon$-aminocaproic acid N-hydroxysuccinimide ester) was from Calbiochem, San Diego, Calif. Streptavidin-agarose was from Bethesda Research Laboratories, Bethesda, Md. The acrylamide gel exclusion column was from Beckman Instruments, Fullerton, Calif.

Preparation of iron-binding proteins

Iron saturation of human transferrin and lactoferrin and preparation of the apoproteins were achieved by methods described previously (A. B. Schryvers and L. Morris, Molecular Microbiology, 2:281–288) except that an additional preparation of apolactoferrin was prepared with the buffers used by Mazurier and Spik (Biochim. Biophys. Acta. 629:399–408.) Protein preparations were concentrated by ultrafiltration with an Amicon Centriflo membrane cone (Amicon Corporation, Danvers, Mass.) prior to sterile filtration through a 0.2 $\mu$m membrane. The iron saturation of the preparations was checked by measuring the absorbance at 465 nm.

Biotinylation of lactoferrin

Preparations of iron-saturated human lactoferrin were equilibrated with 50 mM Tris hydrochloride (pH 7.5) buffer by cycles of gel filtration and ultrafiltration and diluted to 1 mg/ml. 250 $\mu$g of Biotin-X-NHS dissolved in 16 $\mu$l of dimethylformamide was added to each milliliter of the protein solution and the mixture was incubated with gentle agitation at 4° C. for 2 hours. The reaction was stopped by the addition of 100 $\mu$l of 10 mg/ml glycine to each 1 ml portion, and the mixture was incubated for an additional 2 hours with agitation at 4° C. The samples were dialyzed against three changes of 50 mM Tris hydrochloride, pH 8.0, 100 mM NaCl and one change of 50 mM Tris hydrochloride, pH 7.5, concentrated by ultrafiltration with an Amicon Centriflo membrane cone and stored at 4° C.

Preparation of membranes

Cells were harvested and washed in 50 mM Tris hydrochloride, pH 7.5 buffer and resuspended at a concentration of 0.2 g of cells per ml in buffer containing 50 $\mu$g of phenylmethylsulfonyl fluoride per ml. After the cells were lysed by passage two times through a French pressure cell at 16,000 lb/in$^2$, cellular debris was removed by centrifugation at 8,000$\times$g for 15 min. Crude total membranes were collected by centrifugation at 140,000 $\times$g for 1 hour and suspended in the above buffer. Outer membranes were prepared from crude total membranes by selective detergent extraction with "SARKOSYL", a trademark for a series of surface-active N-acylated derivatives NL97. Total membranes were diluted to 5 mg of protein per ml. and "SARKOSYL" was added to 0.5%. The mixture was incubated on ice for 30 min. and the outer membranes were collected by centrifugation at 180,000 $\times$g for 10 min. The pellet was resuspended in buffer and reextracted as above, and the final washed pellet was resuspended in buffer alone.

Batch affinity isolation of binding protein

20 $\mu$g of biotinylated human lactoferrin or transferrin was mixed with 0.75 mg of total membrane protein in 1 ml of 50 mM Tris hydrochloride 100 mM NaCl, pH 8.0 buffer and incubated with gentle agitation for 60 min. at 37° C. The membranes were pelleted by centrifugation at 16,000 $\times$g for 10 min in an Eppendorf microcentrifuge and resuspended in 1 ml of buffer. EDTA was added to 10 mM and "SARKOSYL" was added to 0.75%, followed by 100 $\mu$l of a ½ dilution of streptavidin-agarose (Bethesda Research Laboratories, Bethesda, Md.). After incubation at 22° C. for 60 min. the mixture was centrifuged at 750 $\times$g for 3 min. and the supernatant was removed. The affinity resin pellet was subjected to one of three different washing regimens in which buffers of different compositions were added to the pellet and incubated for 10 min. at 22° C., the mixture was centrifuged as above, and the supernatant was removed. The number of washing steps and the buffer compositions for the different washing methods were as follows. Washing method 1: Wash three times with 50 mM Tris hydrochloride, 100 mM NaCl, pH 8.0 buffer containing 10 mM EDTA and 0.5% Sarkosyl, followed by two washes with buffer without EDTA or detergent. Washing method 2: Wash three times with 50 mM Tris hydrochloride, 1 M NaCl, pH 8.0 containing 10 mM EDTA and 0.5% "SARKOSYL", followed by one wash with the above buffer without EDTA or detergent and a final wash with 50 mM Tris hydrochloride, 100 mM NaCl, pH 8.0. Washing method 3: Wash three times with 50 mM Tris hydrochloride, 1 M NaCl, 250 mM guanidine hydrochloride, pH 8.0 containing 10 mM EDTA and 0.5% "SARKOSYL", followed by one wash with buffer without EDTA or detergent and a final wash with 50 mM Tris hydrochloride, 100 mM NaCl, pH 8.0 buffer. After the final washing step, the pellet was suspended in 200 $\mu$l of sample buffer (0.2 M Tris hydrochloride, pH 6.81, 2% sodium dodecyl sulfate, 30% glycerol, 0.1% bromophenol blue) without reducing reagent and heated at 100° C. for 5 min. to elute bound proteins. After boiling, the sample was quickly cooled on ice for 1 min. and then centrifuged at 750 $\times$g for 3 min. The supernatant was immediately transferred to a separate tube, and beta-mercaptoethanol was added to a final concentration of 1.4 M. A 50 $\mu$l portion of this sample was applied to a 10% SDS-PAGE gel and electrophoresis was performed according to the method of Laemmli (Nature 227:680–685, 1970). The SDS-PAGE gel was silver-stained according to the method of Oakley et al. (Anal. Biochem 105:361-363, 1980) with the following minor modifications. The gel was first fixed overnight with a solution of 25% isopropanol, 7% acetic acid. After removal of the developing solution, development was stopped with a solution of 0.35% acetic acid for 1 hour, and then the gel was washed with water.

Lactoferrin binding assay

The dot-binding assay for lactoferrin was performed essentially as described previously for transferrin-binding activity (A. B. Schryvers and L. Morris, Molecular Microbiology, 2:281-288, 1988) except that conjugated lactoferrin (250 to 500 ng/ml) was included in the binding mixture. The commercially prepared human lactoferrin has a ratio of peroxidase to lactoferrin of 1:1.5. Therefore, the concentration of conjugated lactoferrin used routinely ranged from approximately 1.8 to 3.6 nM (the average molecular weight of conjugated lactoferrin is 140,000). In competition experiments, mixtures of unconjugated proteins and conjugated human lactoferrin were prepared prior to application to the membrane.

For expression experiments requiring quantitation, cell suspensions were adjusted to an $A_{600}$ of 10, and a series of nine two-fold dilutions were prepared and spotted onto the paper. In samples where significant binding protein expression was anticipated, the first dilution was a 10-fold dilution. A dilution series of the conjugated human lactoferrin was also applied directly to the same paper. After development with substrate and drying of the paper, the spots were measured with a BioRad model 620 Video Densitometer by using the reflectance setting and interfaced with a microcomputer with the Bio-Rad 1-D Analyst software package (Bio-Rad Laboratories, Richmond, Calif.). A standard curve was constructed from the areas under the peaks for the dilutions of conjugate. The measured areas under the peak for the dilution of samples were used to determine the amount of conjugate bound. Only peaks whose areas fell within the range of the values used to construct the standard curve were used for calculations. The protein concentration of the cell suspensions, determined by the assay of Lowry et al. (J. Biol. Chem. 193:265-275, 1951), was used to calculate the amount of binding protein bound per milligram of whole cell protein, and the initial $A_{600}$ reading was used to calculate the amount of binding protein expressed per milliliter of culture volume.

Determination of protein concentration

Protein was estimated by the method of Lowry et al. with bovine serum albumin as the standard. Preliminary protein concentration was determined by the rapid method described by Rylatt et al. (Anal. Biochem. 121:213-214, 1982) with bovine serum albumin as the standard and were later verified by the Lowry et al. assay.

TABLE 1

Expression of Lactoferrin-Binding Activity

| Addition(s) (μM) to growth medium[a] | Final $A_{600}$[b] | Binding activity[c] ng/mg | ng/ml |
|---|---|---|---|
| None | 3.8 | <22 | <43 |
| EDDA (40) | 1.8 | 5,800 | 3,300 |
| EDDA (60) | 1.4 | 7,000 | 4,100 |
| EDDA (80) | 1.1 | 7,300 | 3,400 |
| EDDA (100) | 0.9 | 7,600 | 2,700 |
| +FeCl₃ (120) | 3.6 | <30 | <50 |
| +HHb (0.1) | 1.7 | 7,600 | 5,200 |
| +HHb (0.5) | 2.3 | 7,800 | 6,400 |
| +HHb (2.0) | 2.6 | 280 | 330 |
| +HHb (5.0) | 3.7 | <29 | <43 |
| +HHb (20) | 3.8 | <24 | <44 |

TABLE 1-continued

Expression of Lactoferrin-Binding Activity

| Addition(s) (μM) to growth medium[a] | Final $A_{600}$[b] | Binding activity[c] ng/mg | ng/ml |
|---|---|---|---|
| +HTr (1.0) | 1.8 | 7,100 | 4,100 |

[a]Growth medium consisted of brain-heart infusion broth with the indicated additions. HHb. Human hemoglobin: HTr, iron-saturated human transferrin.
[b]Cultures were inoculated with cells resuspended from fresh growth on chocolate plates to a starting $A_{600}$ of 0.04 and incubated at 37° C. for 16 h. The final $A_{600}$ was measured after 16 h growth with medium containing the indicated additions as a blank.
[c]Binding activity expressed as nanograms of conjugated lactoferrin bound per milligram of total cell protein or per milliliter of original culture volume was determined as described in the text.

RESULTS

Expression of lactoferrin-binding activity

To evaluate the regulation of expression of lactoferrin-binding activity in *N. meningitidis*, strain B16B6 was grown in broth containing a variety of different additions. Human lactoferrin conjugated to peroxidase (HRP-lactoferrin) was used to detect lactoferrin-binding activity in intact meningococcal cells. As shown in Table 1, the level of expression of lactoferin-binding activity was low in cells grown in broth alone but was markedly increased by the addition of the synthetic iron chelator EDDA. The increased expression was shown to be due to reduced iron levels, since addition of excess iron resulted in a return to the original low levels of expression. The expression of lactoferrin-binding activity closely paralleled the expression of transferrin-binding activity.

The experiment on the time course of expression of transferrin-binding activity reported in a previous study (FIG. 1 in A. B. Schryvers and L. Morris, Molecular Microbiology, 2:281-288, 1988) was performed in duplicate and the lactoferrin binding assay gave essentially identical results (data not shown). Under these conditions maximal binding activity was attained after 12 to 16 hrs incubation.

The results in Table 1 also show that near-maximal levels of expression were achieved with intermediate levels of added EDDA. The level of lactoferrin binding activity observed in this experiment was comparable to that achieved under more stringent iron-limiting conditions, such as occurred when the cells were exposed to a second iron-limited growth cycle (data not shown). As illustrated in Table 1, provision of complex iron in the form of hemoglobin or human transferrin partially reversed the growth limitation imposed by the high levels of EDDA without dramatically reducing binding activity. However, when higher levels of hemoglobin were added, expression of binding activity was repressed to undetectable levels.

Lactoferrin-binding activity was detected in 20 of 20 meningococcal strains tested (data not shown), which is consistent with previous observations that all meningococcal strains tested were capable of using lactoferrin iron for growth.

Identification of the lactoferrin binding protein

A batch method of affinity chromatography with biotinylated human lactoferrin and streptavidin-agarose was used to identify the lactoferrin-binding protein in several different meningococcal strains. A protein of approximately 105,000 molecular weight was specifically bound to the lactoferrin affinity resin when total membranes from iron-starved *N. meningitidis* B16B6 were used. When biotinylated lactoferrin was omitted from the procedure the band was absent, indicating that specific binding to lactoferrin was involved. The band was also absent when total membranes from iron-sufficient cells were used which is consistent with the observation that expression of lactoferrin-binding activity is strongly repressed by iron (Table 1). Although proteins of 70,000 and 38,000 molecular weight were also observed to copurify with the 105,000 molecular weight band when mild washing was performed, they were successively removed by more extensive washing procedures. Under the conditions of elution, very little biotinylated lactoferrin was released from the resin (80,000 molecular weight), but inclusion of a reducing reagent in the sample mix prior to boiling resulted in an increase in this band observed by SDS-PAGE. A minor band of 37,000 molecular weight was observed in virtually all samples. Affinity chromatography using total membranes from group X and group W135 meningococcal strains identified a lactoferrin-binding protein of a similar molecular weight. The band observed at 70,000 Ml in these samples was due to inadequate washing, and the band at 37,000 was the common contaminating band found in all samples, including controls.

The 105,000 molecular weight protein isolated from total membranes by affinity chromatography corresponded to a high molecular weight protein observed in outer membranes prepared from iron-deficient B16B6. The protein was iron-regulated in B16B6 and in group X. The 70 kilodalton (kDa) protein that copurified with the 105 kDa lactoferrin-binding protein migrated at the position of a predominant protein found in outer membranes from iron-deficient B16B6. The protein was iron-regulated in B16B6 and in group X. This protein was distinct from a transferrin-binding protein in B16B6 identified previously which was the lower protein band isolated by using biotinylated transferrin. The lower-molecular weight transferrin binding protein varied in molecular weight between different meningococcal strains and was the only protein which retained binding activity after SDS-PAGE and electroblotting. In addition to the lower molecular weight binding protein isolated with biotinylated transferrin, these samples contained a high molecular weight binding protein and biotinylated transferrin (band at 80 kDa) which was released during the boiling step. The separation of the 70 kDa protein and the lower molecular weight transferrin-binding protein in strain B16B6 was optimized in an 8 to 10% gradient gel, but these proteins co-migrated on standard 10% acrylamide SDS-PAGE gels.

EXAMPLE 2

Purification of Human Transferrin or Human Lactoferrin Receptors and Incorporation into Vaccine Preparations (a) Preparation of Iron-deficient Total Membranes Meningococcal cells resuspended from fresh cultures on chocolate plates were used to inoculate prewarmed Brain Heart Infusion broth containing 100 $\mu$M EDTA to a starting $A_{600}$ of 0.02. The resulting culture was incubated at 37° C. with shaking for 16 hrs prior to harvest by centrifugation at 9,000×g for 15 minutes. The cells were resuspended to 0.2 gm/ml in 50 mM TrisHCl, pH 8 buffer containing 50 $\mu$g/ml phenylmethylsulfonyl fluoride. The cells were lysed by passing the suspension through a French pressure cell at 16,000 lb/in$^2$ and cell debris was removed by centrifugation at 9,000×g for 15 min. Crude total membranes were collected by centrifugation at 140,000×g for 1 hr and resuspended in 50 mM TrisHCl, pH 8 buffer.

(b) Affinity Isolation of Receptor Proteins 0.9 mg of biotinylated human transferrin or biotinylated human lactoferrin prepared as described in Example 1 was mixed with 72 mg of crude total membrane protein in 60 mls of 50 mM TrisHCl, 100 mM NaCl, pH 8 buffer and incubated for 1 hr at 22° C. The mixture was centrifuged at 9,000×g for 15 minutes to collect the membranes and the pellet was resuspended in 60 mls of the above buffer and incubated for 10 minutes at 22° C. EDTA was added to 10 mM and "SARKOSYL" was added to 0.75% and the mixture was incubated a further 10 minutes at room temperature prior to centrifugation at 9,000×g for 15 min. The supernatant was mixed with 5 mls of Streptavidin-Agarose (1-2 mg streptavidin per ml resin) and incubated at room temperature with gentle mixing for 1 hr. The resin was collected by centrifugation at 500×g for 10 minutes and resuspended in 80 mls of 50 mM TrisHCl, 1 M NaCl, 10 mM EDTA, 0.75% "SARKOSYL", pH 8 buffer. The resin was again collected by centrifugation and washed two more times in the above buffer. After the final wash the resin was resuspended in 20 mls of the above buffer and poured into a 1 cm diameter chromatography column. The packed resin was washed with an additional 10 mls of 50 mM TrisHCl, 1 M NaCl, 10 mM EDTA, 0.5% "SARKOSYL" and the receptor proteins were eluted by application of a 60 ml gradient of 0 to 3 M guanidine hydrochloride in 50 mM Tris HCl, 1M NaCl, 10 mM EDTA, 0.05% "SARKOSYL". The fractions containing receptor proteins were pooled and dialyzed against two changes of 3 liters of 50 mM TrisHCl, pH 7.5 buffer and one change of phosphate buffered saline (50 mM sodium phosphate, 150 mM NaCl, pH 7.4) and concentrated by ultrafiltration to a final volume of 1 ml.

(c) Preparation of Vaccine

100 $\mu$g of the purified receptor proteins in 1 ml of phosphate buffered saline was diluted to 2.5 ml in phosphate buffered saline containing 0.01% MERTHIOLATE, sterilized by passage through a 0.2 $\mu$m filter and transferred aseptically to a sterile vial. A sterile preparation of 20 mg of aluminum hydroxide in phosphate buffered saline was added to each vial prior to use. Alternatively, for animal studies, 50 $\mu$g of muramyl dipeptide in 50 $\mu$l of normal saline was added.

Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A transferrin receptor protein isolated and purified from a bacterial pathogen containing the same, produced by the process which comprises isolating a membrane preparation from a bacterial strain expressing transferrin-binding activity and purifying said transferrin receptor protein from the membrane preparation by an affinity method involving the sequential steps of prebinding of transferrin to transferrin receptor protein in the membrane of the bacterial pathogen, solubilizing the membrane, immobilizing the transferrin and separating the transferrin receptor protein from the immobilized transferrin.

2. The transferrin receptor protein as claimed in claim 1 wherein the bacterial pathogen is selected from the group consisting of *Neisseria meningitidis, Neisseria gonorrhoeae, Haemophilus influenzae, Branhamella catarrhalis, Pasteurella haemolytica, Haemophilus somnus, Pasteurella multocida* and *Actinobacillus pleuropneumoniae.*

3. The transferrin receptor protein as claimed in claim 1 wherein the bacterial pathogen is *Neisseria meningitidis.*

4. The transferrin receptor protein as claimed in claim 1 wherein the solubilization is conducted using a detergent and the immobilization is conducted by binding of biotinylated transferrin by streptavidin-agarose.

5. A transferrin receptor protein isolated and purified form a bacterial pathogen containing the same, wherein said transferrin receptor protein has a lower molecular weight in the range of about 58,000 to about 98,000 daltons or a higher molecular weight in the range of about 94,000 to about 106,000 daltons, wherein said molecular weight is determined by sodium dodecyl sulphate polyacrylamide gel electrophoresis.

6. The transferrin receptor protein as claimed in claim 5 wherein the bacterial pathogen is selected from the group consisting of *Neisseria meningitidis, Neisseria gonorrhoeae, Haemophilus influenzae, Branhamella catarrhalis, Pasteurella haemolytica, Haemophilus somnus, Pasteurella multocida* and *Actinobacillus pleuropneumoniae.*

7. The transferrin receptor protein as claimed in claim 5 wherein the bacterial pathogen is *Neisseria meningitidis.*

8. A vaccine which provides protective immunity against a bacterial pathogen, said vaccine comparing an effective amount to provide protective immunity against a bacterial pathogen, of a transferrin receptor protein as purified and isolated from said pathogen as set forth in claim 1 and a pharmaceutically acceptable carrier therefor.

9. The vaccine of claim 8 further comprising sodium chloride, sodium phosphate, buffer and "MERTHIOLATE".

10. The vaccine of claim 8 further comprising an adjuvant.

11. The vaccine of claim 10 wherein said adjuvant is aluminum hydroxide.

12. A vaccine which provides protective immunity against a bacterial pathogen, said vaccine comparing an effective amount to provide protective immunity against a bacterial pathogen of a transferrin receptor protein obtained from said bacterial protein as claimed in claim 5 and a pharmaceutically acceptable carrier therefor.

13. The vaccine as claimed in claim 12 comprising sodium chloride, sodium phosphate, buffer and thimersol.

14. The vaccine as claimed in claim 12 comprising an adjuvant.

15. The vaccine as claimed in claim 14 wherein said adjuvant is aluminum hydroxide.

* * * * *